(12) United States Patent
Karger et al.

(10) Patent No.: US 8,580,570 B2
(45) Date of Patent: Nov. 12, 2013

(54) NARROW BORE POROUS LAYER OPEN TUBE CAPILLARY COLUMN AND USES THEREOF

(75) Inventors: Barry L. Karger, Newton, MA (US); Jian Zhang, Plainsboro, NJ (US)

(73) Assignee: Northeastern University, Boston, MA (US)

( * ) Notice: Subject to any disclaimer, the term of this patent is extended or adjusted under 35 U.S.C. 154(b) by 136 days.

(21) Appl. No.: 13/184,075

(22) Filed: Jul. 15, 2011

(65) Prior Publication Data
US 2011/0290009 A1 Dec. 1, 2011

Related U.S. Application Data

(63) Continuation of application No. 12/306,232, filed as application No. PCT/US2007/014398 on Jun. 20, 2007, now abandoned.

(60) Provisional application No. 60/815,314, filed on Jun. 21, 2006.

(51) Int. Cl.
*G01N 30/00* (2006.01)
*G01N 30/02* (2006.01)

(52) U.S. Cl.
USPC ............... 436/161; 436/52; 436/807; 422/54; 422/70; 422/78

(58) Field of Classification Search
USPC ................... 436/52, 807, 161; 422/54, 70, 78
See application file for complete search history.

(56) References Cited

U.S. PATENT DOCUMENTS

| | | | |
|---|---|---|---|
| 4,962,042 A * | 10/1990 | Morabito et al. | 436/161 |
| 6,207,049 B1 | 3/2001 | Abdel-Rahman | 210/198.2 |
| 6,484,560 B1 * | 11/2002 | Prest | 73/23.41 |
| 2003/0068825 A1 * | 4/2003 | Washburn et al. | 436/86 |
| 2004/0200776 A1 | 10/2004 | Ivano et al. | |
| 2005/0274662 A1 | 12/2005 | Xie et al. | |

OTHER PUBLICATIONS

Huang et al., J. of Chromatogr. A, 858 (1999) 91-101.*
Tomer et al., Mass Spectrometry Reviews, Capillary Liquid Chromatography Mass Spectrometry, 1994, 13, 431-457.*
Callister, W.D.; Fundamentals of Materials Science and Engineering: An Integrated Approach, 2nd Edition, 2005, John Wiley & Sons, Inc., Appendix E, A39.
Huang et al., Capillary electrochomatography of proteins and peptides with porous-layer open-tubular columns, Journal of Chromatography A, 858 (1999) 91-101.

* cited by examiner

*Primary Examiner* — David C Mellon
*Assistant Examiner* — Allison M Gionta
(74) *Attorney, Agent, or Firm* — McLane, Graf, Raulerson & Middleton, PA

(57) ABSTRACT

A polymer-based PLOT capillary column prepared by in situ copolymerization of a functional monomer, which usually contains the retentive chemistries, and a crosslinking monomer, which enhances the strength of the polymer matrix, is disclosed. Also disclosed is a system comprising the polymer-based PLOT column coupled to a mass flow or concentration sensitive detector, for carrying out a chemical analysis method on samples separated by liquid chromatography using the column, and a process for using the system. Columns of the invention can be prepared in a robust fashion with a very narrow i.d., e.g., 5-15 μm. Thus, they are suitable for commercial use in ultratrace LC/MS proteomic analysis. Columns according to the invention are characterized by high resolving power and high column-to-column reproducibility. When these columns are coupled on-line with, e.g., ESI-MS detection, the resulting systems are capable of detecting the component parts of complex proteomic samples down to the low attomole to sub-attomole level.

13 Claims, 13 Drawing Sheets

NARROW BORE POROUS LAYER OPEN TUBE CAPILLARY COLUMN AND USES THEREOF

CROSS REFERENCE TO RELATED APPLICATIONS

The present application is a continuation application of and claims priority from U.S. application Ser. No. 12/306,232, filed Dec. 22, 2008, which is a 371 of International Application No. PCT/US2007/014398, filed Jun. 20, 2007, which claims the priority of U.S. Provisional Patent Application No. 60/815,314, filed on Jun. 21, 2006, the whole of both of which are hereby incorporated by reference herein.

STATEMENT REGARDING FEDERALLY SPONSORED RESEARCH OR DEVELOPMENT

Part of the work leading to this invention was carried out with United States Government support provided under a grant from the National Institutes of Health, Grant No. GM-15847. Therefore, the U.S. Government has certain rights in this invention.

BACKGROUND OF THE INVENTION

Electrospray ionization-mass spectrometry (ESI-MS) has become a routine tool in proteomic studies, primarily due to its high sensitivity, broad dynamic range, and versatility for online coupling with capillary high performance liquid chromatography (HPLC)[1-3]. High-resolution separation prior to MS detection allows complex mixtures to be characterized by extending both the dynamic range and detection level achievable in the analysis. Capillary LC, using 75-150 μm i.d. reversed-phase columns, offers the advantages of high resolving power, high mass sensitivity, and low sample and mobile phase consumption, and hence are widely used today. However, even with such columns, LC-MS analysis of very low quantity samples (e.g., cells from small tissue samples obtained using laser capture microdissection[4]) can still be problematic. More sensitive proteomic analysis methods are necessary to tackle many challenging biological problems.

For a given injected sample amount, narrow-bore columns result in reduced chromatographic band dilution, the analytes being eluted in a smaller volume at a higher concentration. In addition, the volumetric flow rate is an important parameter influencing ESI sensitivity[5-10]. Low flow rates resulting from the narrow bore columns lead to smaller electrospray droplet sizes, thus enhancing analyte ionization efficiency and reducing the effect of ion suppression, all leading to higher sensitivity. Additionally, the electrospray emitter attached to such a low flow rate column can be placed nearer to the MS inlet than in comparable configurations, which improves the sampling efficiency at low flow rates. NanoESI, at flow rates of <30 nL/min, will, thus, significantly increase the MS response compared to conventional flow rates (>300 nL/min)[5,6,11]. On the other hand, packing narrow-bore (<20 μm i.d.) columns with conventional microparticles can be technically difficult because the decreased ratio of column i.d. to particle size induces more frequent column clogging, and packing microparticles into narrow-bore (<20 μm i.d.) columns requires ultrahigh packing pressure (usually >10,000 psi) and special instrumentation. Generally, the ratio of column i.d. to particle size should be greater than 10 to pack dense columns reproducibly. Recently, the preparation of 10 μm i.d. columns packed with 1.0 μm non-porous particles at extremely high pressure has been reported[12]. The back pressure of a 30 cm long column can reach as high as 100,000 psi at the optimum linear velocity of 0.4 cm/s. Monolithic capillary columns are increasingly considered as a viable alternative to microparticle-packed columns because of their moderate back pressure and high resolving power[6,8,13-16]. It was recently demonstrated that low-attomole sensitivity can be achieved at a flow rate of 20 nL/min using a 20 μm i.d. PS-DVB monolithic column[6]. Even more recently, others have reported on the preparation of 20 and 10 μm i.d. silica-based monolithic columns[8,16], demonstrating sensitive and quantitative proteomic analyses at the very low flow rate of 10 nL/min[16]. However, in all these cases, preparation of the monolithic columns was difficult, in part due to the increased surface area to column i.d. ratio.

Given the excellent performance of open tubular capillary gas chromatography (GC), researchers have for many years tried to implement such columns for LC. It was recognized early on[49] that very narrow bore columns of 5-10 μm i.d. were necessary for open tubular LC, in order to overcome band broadening due to the laminar flow in the capillary tube. Approaches of coating the capillary tubing using silicone[17] or chemical modification of etched surfaces[18] were first developed to prepare open tubular capillary LC columns. However, such columns provided low retention and low sample loading capacity even for small molecules, let alone for complex biological samples.

Porous layer open tube (PLOT) columns were introduced in 1960s to increase the sample loading capacity of the GC columns[19]. Although efforts have been made in the last 20 years to prepare PLOT capillary LC columns[20-23], success has been limited due in part to the following: 1) lack of a sensitive, universal, small dead volume detector[24]; 2) lack of ability to generate effective gradient elution at very low flow rates; and 3) difficulties in the preparation of capillary columns with a uniform stationary layer reproducibly. ESI-MS has proven to be an ideal sensitive detector with zero dead volume, and current HPLC pumps can provide stable flow rate at low nL/min level after accurate splitting. The remaining problem is to prepare and implement high efficiency LC PLOT columns, a major challenge being to cast a suitably uniform porous layer on the column to provide sufficient retention and sample loading capacity. Several methods have been developed to realize a retentive layer suitable for increasing the surface area and phase ratio, e.g., static[25], dynamic[26,27], and precipitation coating[28]. To simplify the preparation process, a method of laying down a porous siliceous layer in a single step via a sol-gel process was described[29]. Methods of preparing gold nanoparticle-coated PLOT columns have also been described[30,31]. However, these and other attempts[32-36] have not been sufficiently successful to permit commercial level development of PLOT capillary LC columns and their use, e.g., in ESI-MS.

BRIEF SUMMARY OF THE INVENTION

A new polymer-based PLOT column prepared by in situ copolymerization of a functional monomer, which usually contains the retentive chemistries, and a crosslinking monomer, which enhances the strength of the polymer matrix, is disclosed herein. For example, styrenic based monomers such as styrene and divinylbenzene or meth/acrylic based monomers such as butyl or stearyl methacrylate and ethylene glycol dimethacrylate, are employed. Columns of the invention can be prepared in a robust fashion with a very narrow i.d., e.g., 5-15 μm. Thus, they are suitable for commercial use in ultratrace LC/MS proteomic analysis. Columns according to the invention are characterized by high resolving power and high column-to-column reproducibility. When these columns are coupled on-line with, e.g., ESI-MS detection, the resulting systems according to the invention are capable of detecting the component parts of complex proteomic samples down to the low attomole to sub-attomole level. The power of methods using columns of the invention is demonstrated in particular by coupling such columns to the new mass spectrometers, such as the hybrid linear ion-trap/FT mass spectrometer (LTQ/FT-MS, ThermoElectron, San Jose, Calif.), for bioanalyses. The high resolution and sensitivity of these columns opens up major possibilities for the diagnosis of biopsy samples as well as the determination of specific biomarkers that can provide molecular phenotyping of individual samples. Such developments are of clear clinical importance and therapeutic significance in that tissue samples of a highly limited quantity can be successfully analyzed for proteomic content using the columns and methods of the invention. Also, columns according to the invention can be online coupled to other sensitive detectors such as fluorescence, electro/chemiluminence or nuclear magnetic resonance (NMR) for, e.g., detection of trace chemical or biological agents in chemical or biological defense applications.

Thus, in one aspect, the invention is directed to a porous layer open tube capillary column, or channel in a microfabricated device, the column or channel including a capillary column or channel having an i.d. of 15 μm or less (preferably 10 μm or less); and a rigid porous layer separation medium comprising a highly crosslinked, macroporous, organic polymeric stationary phase layer attached covalently to the inner wall surface of the column or channel, wherein the organic polymeric stationary phase layer includes styrenic, methacrylic or acrylic monomeric units, or combinations thereof; wherein the organic polymeric stationary phase layer is from 0.5-3 μm in thickness; wherein the organic polymeric stationary phase layer is thermally stable to 250° C.; and wherein the reproducibility of retention time on comparable columns or channels during use varies less than 10%, and, preferably less than 5%. A preferred capillary column according to the invention has a length of greater than or equal to one meter, and preferably greater than or equal to three meters. In preferred embodiments of the capillary column or channel, the organic polymeric stationary phase layer is poly(styrene-divinylbenzene) or has (C4-C18) alkyl methacrylate monomer units, and the column or channel during use for liquid chromatography has a flow rate at 6000 psi or less of 5-50 nL/min.

In another aspect, the invention is directed to method of preparing a separation capillary column or channel in a microfabricated device, the column or channel comprising a porous layer open tube separation medium including a macroporous, organic polymeric stationary phase layer, said method including the steps of (1) providing an unfilled capillary column, or channel in a microfabricated device, the column or channel being open at both ends thereof and having an i.d. of 15 μm or less, the inner wall surface of the column or channel including a bifunctional anchoring or coupling agent suitable for covalent attachment of a macroporous, organic polymeric stationary phase layer as a porous layer open tube separation medium; (2) adding to the column or channel a mixture including a functional monomer selected from the group consisting of styrenic, methacrylic and acrylic monomers, and combinations thereof; a crosslinker compatible with the functional monomer, the crosslinker being capable of providing extensive crosslinking; a polar porogenic solvent; and an initiator for thermal or UV induced polymerization; and (3) polymerizing the mixture in the column to form the macroporous, organic polymeric stationary phase layer as the porous layer open tube separation medium attached to the inner surface of the column or channel. In preferred embodiments of the method of the invention, the inner wall surface of the column or channel is silica and the bifunctional anchoring or coupling agent contains at one end a functional group reactive with silica and at the other end a functional group reactive with said functional monomer (an exemplary bifunctional anchoring or coupling agent being 3-(trimethoxysilyl)propyl methacrylate); the functional monomer in the polymerization mixture is styrene and the crosslinking agent is divinylbenzene. In other preferred embodiments of the method, the functional monomer in said polymerization mixture is methacrylate (e.g., (C4-C18) alkyl methacrylate, in particular, butyl or stearyl methacrylate), and the preferred crosslinking agent is ethylene glycol dimethacrylate. Preferred porogenic solvents include $C_nH_{2n+1}OH$, wherein $1 \leq n \leq 4$), wherein ethanol is particularly preferred, or acetonitrile. In other preferred embodiments of the method, the ratio of total monomer (functional monomer plus crosslinking monomer) to porogenic solvent in the polymerization mixture varies between 10-40% (V/V) while the ratio of functional monomer to crosslinking monomer varies between 1:1 to 1:3.

In another aspect, the invention is directed to a process of carrying out a chemical analysis method including the steps of providing the separation capillary column or channel of the invention; coupling the column or channel to a mass flow or concentration sensitive detector; applying an aliquot of a liquid sample to the column or channel; conducting a liquid chromatographic separation procedure on the applied sample; and detecting the separated sample with the detector to carry out the chemical analysis method.

In yet another aspect, the invention is directed to a system for carrying out a chemical analysis method, the system including the separation capillary column or channel of the invention and a concentration sensitive detector coupled with an interface to the exit end of the separation column or channel. Exemplary concentration sensitive detectors include a mass spectrometer, a fluorescence detector, an electro-chemiluminescence detector and a nuclear magnetic resonance detector. A preferred interface is an electrospray ionization (ESI) interface or a matrix assisted laser desorption ionization (MALDI) interface. In a preferred embodiment, the system of the invention further includes a preparatory precolumn coupled to the entrance end of the separation column or channel.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings, in which:

FIG. 5A is the base peak chromatogram from the microSPE-nanoLC-ESI-MS analysis of a 4 ng tryptic in-gel digest of a single SDS-PAGE cut of M. Acetivorans and FIG. 5B shows extracted ion chromatograms of six high intensity peaks used to calculate the peak capacity.

DETAILED DESCRIPTION OF THE INVENTION

Figure 1:
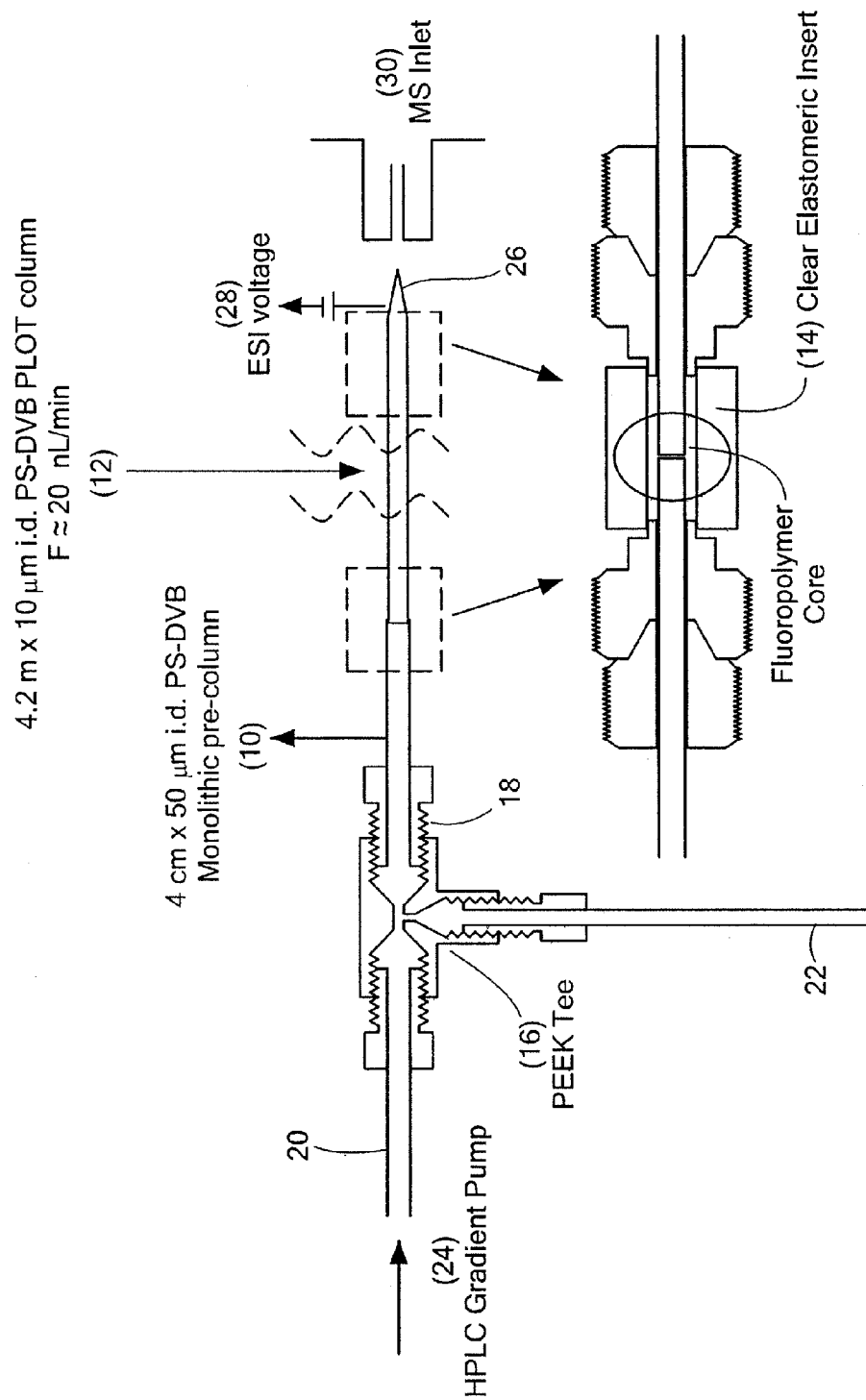
FIG. 1 is a schematic diagram of an exemplary embodiment of a 10 μm i.d. poly(styrene-divinylbenzene) PLOT column according to the invention in a microSPE/nanoLC/ESI-MS system according to the invention.

According to the invention, high-efficiency, narrow, e.g., 10 μm i.d., PLOT columns (e.g., poly(styrene-divinylbenzene) can be repeatedly prepared in a single copolymerization step. The polymer layer is covalently attached to the walls of the capillary, and there is thus no need for column frits. Column-to-column retention time reproducibility is ~3% RSD, and, in terms of relative retention time, ~2% RSD. The high permeability of the open structure allows long columns to be used at moderate pressure, which aids sample loading capacities. The concentrated analyte that elutes from a PLOT column according to the invention, combined with decreased ion suppression and enhanced ion collection efficiency at a flow rate of, e.g., 20 nL/min, significantly improves ESI-MS sensitivity. Due to its open porous layer structure, the PLOT column of the invention demonstrates high efficiency for the separation of large peptides, as well as peptides with phosphorylated and glycosylated modifications. The columns are well suited to extended range proteomic analysis. The high resolution capabilities of the column have been demonstrated in an exemplary system described herein employing micro-solid phase extraction, nano-liquid chromatography, electro-spray interface, mass spectrometry (microSPE-nanoLC-ESI-MS) analysis of a complex proteome sample using a 4.2 m×10 μm i.d. PS-DVB PLOT column coupled with a 50 μm i.d. PS-DVB monolithic precolumn.

Preferred embodiments of the columns according to the invention use different retentive chemistry functionalities compared to the prior art and a very high degree of crosslinking to prepare the inside wall layer (stationary phase) so that the stationary phase is essentially rigid. This means that there is essentially no swelling of the stationary phase, and, consequently, no change in volume, in the presence of the mobile phase, which usually contains organic solvent. These changes have led to dramatic improvements in the resolution and reproducibility of analyses carried out using columns according to the invention because, without swelling of the stationary phase, the kinetics of diffusion of the separating components in and out of the stationary phase is more favorable, that is, mass transfer resistance is minimized, and, thus, high performance is achieved as well as good reproducibility.

With a 10-15 μm i.d. capillary, a PLOT column having an inside wall layer thickness of ~1-3 μm will reduce the open tube i.d. to roughly 7-8 μm. This column diameter has previously been shown to be sufficient to minimize radial band broadening, leading to high performance separations. In addition, commercial HPLC pumps will be able to deliver sufficient flow by virtue of the open tube structure. One point of significance for such a column when coupled to ESI/MS is that the flow rate will be in the range of 5-50 nL/μm, more than an order of magnitude lower than results with 75 μm i.d. columns. From the early days of nano-ESI, it has been recognized that such low flows lead to a significant reduction in ESI droplet size such that only one ion is encapsulated in one droplet. In this case, the significant problem of ion suppression is minimized or eliminated, a feature particularly favorable to peptides with post-translational modifications, such as carbohydrates or phosphates.

The reversed phase PLOT column according to the invention, e.g., 10 μm i.d., yields robust high resolution separation with minimal ion suppression. Use of such columns would significantly impact peptide quantitation and, therefore, yield more comprehensive and accurate results for, e.g., biomarker studies.

The invention is directed to a procedure to reproducibly prepare ultra-narrow bore (i.d. <15 μm) porous layer open tube (PLOT) capillary columns for liquid chromatography coupled with mass spectrometry or other sensitive detection techniques such as fluorescence, electro/chemiluminence or NMR detection. The invention is also directed to the resulting columns and to their uses. In columns according to the invention, the retentive stationary phase is a porous polymer formed by, e.g., temperature induced or UV light induced solution polymerization.

Exemplary uses of PLOT columns according to the invention include high-sensitive, high-efficiency gradient and isocratic single or multi-dimensional nano-LC analysis of limited amounts of biological or medical samples by coupling the columns at low flow rates to mass flow-sensitive detectors (i.e., ESI-MS). Single, parallel or sequential sample separation experiments using PLOT columns according to the invention can be coupled to electrospray ionization mass spectrometry (ESI-MS) or matrix assisted laser desorption ionization mass spectrometry (MALDI-MS).

One embodiment of the method according to the invention is characterized in that the inner surface of the bare fused-silica capillary is pre-functionalized before polymerization with, e.g., an anchoring silane, which contains acryl or meth-acryl groups, enabling the reaction of the anchoring silane with monomers and crosslinkers thereafter.

In another embodiment of this method, the polymerization solution is composed of a functional monomer, such as styrene or alkyl methacrylate; a crosslinker that provides a high degree of crosslinking, such as divinylbenzene or ethylene glycol dimethacrylate, at a typical quantity ratio of monomer/crosslinker of 1:1; and a polar porogenic solvent (or porogen), such as ethanol, methanol, propanol or acetonitrile. The porogen chosen is one that has a negligible swelling effect on the resulting polymer formed and not one that would be a good solvent for the resulting polymer, such as the non-polar solvents toluene, chloroform, tetrahydrofuran or heptane. The polymerization solution has a low viscosity; thus, it can be introduced into the pre-functionalized fused-silica capillary under low pressure, such as 100-psi or lower, for a capillary tubing length of several meters. The retentive layer thus formed using the monomers and crosslinkers described above is ready for chromatographic separation without additional surface functionalization steps.

Another embodiment of this method is characterized in that the polymeric retentive layer, e.g., 0.5-3 μm thick, formed after polymerization is integrated to the fused silica capillary inner wall. The layer's structure is rigid and characterized by a rugulose inner surface, which enhances surface area and, thus, loading capacity.

Another embodiment of the method according to the invention is characterized in that no evaporation of the porogenic solution is needed after polymerization, in contrast to other methods. The porogen is simply flushed out of the column after polymerization. Avoiding the use of a swelling porogen, such as toluene, chloroform, tetrahydrofuran, etc., which may remain in the network after polymerization and thus necessitate an evaporation step, diminishes the problem of clogging during the evaporation step, thus simplifying preparation and improving reproducibility.

In future developments, long columns up to 10 m in length are envisioned, which can be used to improve the resolving power of the system further, still using a conventional LC pumping system. Furthermore, short PLOT columns run at high temperature will be useful for fast separation and analysis. Although, the retentive layer described above can be used for chromatography separation without additional surface functionalization steps (as this retentive layer contains no reactive groups, being devoid of charged functionalities such as sulfonic, carboxylic, primary, secondary, tertiary and quaternary amines), PLOT columns with different surface chemistries for various separation modes can be easily prepared using specific monomers. For example, a more hydrophobic column could be prepared by using stearyl methacrylate instead of styrene, or 2-acrylamido-2-methyl-1-propane sulfonic acid for ion exchange chromatography. Other retentive groups, if desired, could include alkyl chains, hydrophilic groups or affinity functions.

An exemplary column according to the invention is a long, high-efficiency polystyrene-divinylbenzene (PS-DVB), 10 μm i.d. porous layer open tube (PLOT) capillary column. Repeatable PLOT capillaries according to the invention (~3% RSD column-to-column), with high permeability, were easily prepared by in-situ polymerization. Relatively high loading capacities, ~100 fmol for angiotensin I and ~50 fmol for insulin were obtained with a 4.2 m×10 μm i.d. PLOT column. Low detection levels (attomole to sub-attomole) were achieved when the column was coupled on-line with a linear ion trap MS (LTQ). Analysis of human epidermal growth factor receptor (EGFR), a large trans-membrane tyrosine kinase receptor with heterogeneous phosphorylation and glycosylation structures, was obtained at the 25 fmol level. The PLOT column yielded a peak capacity of ~400 for the separation of a 4 ng complex tryptic digest mixture when the sample preparation included a 50 μm i.d. PS-DVB monolithic precolumn and ESI-MS detection. As an example of the power of the column, 3046 unique peptides covering 566 distinct *Methanosarcina acetivorans* proteins were identified from a 50 ng in-gel tryptic digest sample combining five cuts in a single LC/MS/MS analysis using the LTQ. The results demonstrate the potential of the PLOT column according to the invention for high resolution LC/MS at the ultratrace level.

The following examples are presented to illustrate the advantages of the present invention and to assist one of ordinary skill in making and using the same. These examples are not intended in any way otherwise to limit the scope of the disclosure.

Materials

Fused silica capillary tubing with a polyimide outer coating was purchased from Polymicro Technologies (Phoenix, Ariz.). Styrene, divinylbenzene (DVB), ethanol, formic acid (HPLC grade), 3-(trimethoxysilyl)propyl methacrylate, 2,2'-diphenyl-1-picrylhydrazyl (DPPH), N,N-dimethylformamide (DMF) anhydrous, and 2,2'-azobisoisobutyronitrile (AIBN) were obtained from Sigma-Aldrich (St. Louis, Mo.). Acetonitrile (HPLC grade) and deionized water (HPLC grade) were purchased from Fisher Scientific (Fair Lawn, N.J.). A standard tryptic digest of bovine serum albumin (BSA) was from Michrom Bioresources, Inc. (Auburn, Calif.). Angiotensin I, insulin from bovine pancreas, HPLC standard protein mixture (ribonuclease A (13700 Da), cytochrome C (12327 Da), apomyoglobin (17600 Da), holo-transferrin (>70000)), β-casein from milk and human epidermal growth factor receptor (EGFR) from an A431 cancer cell line were purchased from Sigma-Aldrich (St. Louis, Mo.). *Achromobacter* protease I (Lys-C) was obtained from Waco Chemical Co. (Osaka, Japan), and trypsin (sequencing grade) was from Promega (Madison, Wis.).

Example I

Preparation and Characterization of a PLOT column According to the Invention

Fused-silica capillary tubing with a 10 μm i.d. (~5 meters) was first flushed overnight with 1.0 mol/L NaOH at ~1000 psi, washed with water and flushed with 1.0 mol/L hydrochloric acid, and then washed again with water and acetonitrile. The capillary was dried with nitrogen at ~1000 psi to remove residue water and acetonitrile. 30% (v/v) 3-(trimethoxysilyl) propyl methacrylate and 0.5% (wt/v) 2,2'-diphenyl-1-picrylhydrazyl (DPPH) in N,N-dimethylformamide anhydrous (DMF) was freshly prepared and filled into the 10 μm i.d. pretreated capillary. Both ends of the capillary were sealed with a septum, and the capillary was placed in an oven at 110° C. for 6-10 h. The capillary was washed with acetonitrile and blown dry with nitrogen at 1000 psi. A polymerization solution was prepared containing of 5 mg of AIBN, 200 μL styrene, 200 μL DVB, and 600 μL ethanol. The solution was degassed by ultrasonication for 5 min and then filled into the silanized capillary. Both ends of the capillary were sealed with septa, and the capillary was heated at 74° C. for ~16 h in a water bath. The column was then washed with acetonitrile and was ready for use. In addition, 50 μm i.d. PS-DVB monolithic precolumns were prepared using protocols described previously[14].

HPLC separations were performed using a Surveyor pump (ThermoElectron, San Jose, Calif.). Mobile phase A (0.1% (v/v) formic acid in water) and mobile phase B (0.1% (v/v) formic acid, 10% (v/v) water in acetonitrile) were used for the gradient separation. Samples were either bomb loaded onto the PLOT column or onto a 4 cm×50 μm i.d. PS-DVB monolithic precolumn. A microSPE/nanoLC/ESI-MS system using a 10 μm i.d. PLOT column is shown in FIG. 1. Referring now to FIG. 1, in one embodiment, samples are first loaded manually off-line onto a precolumn 10, which is then inverted and butt-to-butt connected to a 10 μm i.d PLOT column 12 using a Picoclear™ fluoropolymer core, clear elastomeric insert connector 14 (New Objective, Woburn, Mass.). The sample is back-flushed from precolumn 10 onto PLOT column 12. A PEEK tee (Upchurch Scientific Inc., Oak Harbor, Wash.) is used as a splitter 16, and the precolumn 10/PLOT column 12 assembly is attached to arm 18 of the splitter. Gradient flow from an HPLC pump 24 is applied through in-line arm 20 of the splitter, and a portion of the gradient flow goes through the 90° splitting arm 22, where a 50 μm i.d. fused silica capillary can be connected to adjust the mobile phase flow through the microSPE-LC assembly. Flow rates of the PLOT column were measured by connecting 50 μm i.d. open fused-silica capillary tubing to the exit end of the PLOT column, and then the volume of mobile phase that flowed for a given period of time was determined.

NanoESI-MS was performed on an LCQ Deca XP or an LTQ ion trap mass spectrometer (ThermoElectron). Referring again to FIG. 1, PLOT column 12 was carefully butt-to-butt connected to a coated ESI spray tip 26 (360 μm o.d., 20 μm i.d. fused silica with 5 μm i.d. tip, 2-3 cm in length, New Objective) using a Picoclear™ connector 14. Electrospray voltage 28 was applied directly on the spray tip 26 to direct droplets of generated sample ions to the MS inlet orifice 30. The data generated from LC/MS experiments were analyzed using standard database searching algorithms (SEQUEST). Peptides were assigned based upon a Peptide Prophet probability greater than 0.95, a $\Delta Cn$ greater than 0.10, and Xcorr greater than 1.8, 2.5 and 3.5 for singly, doubly and triply charged ions, respectively.

In addition to a tryptic digest sample of BSA, Lys-C digests of β-casein and EGFR and an in-gel tryptic digest of *Methanosarcina acetivorans* were used as test mixtures to evaluate the performance of the nanoLC-ESI-MS. Lys-C digestion of β-casein was performed as follows: Lys-C was spiked into the β-casein (at 10 pmole) in a 1:40 (w/w) ratio and incubated for 4 h at 37° C. (pH 8.5). For Lys-C digestion of EGFR, 10 μg lyophilized powder of EGFR was dissolved in 100 μL of 6 M guanidine hydrochloride and 0.1 M ammonium bicarbonate in water. Reduction was conducted with 40 mM dithiothreitol for 30 min at 37° C., followed by alkylation with 80 mM of iodoacetamide for 1.5 h in the dark at room temperature. The buffer was subsequently exchanged to 0.1 M ammonium bicarbonate buffer, pH 8.5, to remove additional salts and reagents. Lys-C (1:20 w/w) was added to digest the protein for 4 h at 37° C. (pH 8.5). The mixture was acidified with 1% formic acid to quench the digestion, followed by storage at −20° C.

*M. acetivorans* cells, grown in methanol, were cultured as previously described[37]. Protein extraction, SDS-polyacrylamide gel electrophoresis (PAGE) fractionation and in-gel digestion were performed using protocols reported previously[37]. The concentration of the whole-cell protein extracts, determined by the Bradford assay (Bio-Rad, Hercules, Calif.), was 3.0 mg/mL. Roughly 45 μg of total protein was loaded on the gel, and after electrophoresis, the gel lanes were cut into 5 fractions. The in-gel tryptic digest of a fraction of *M. acetivorans* proteins (M>70 kDa) was used to evaluate the performance of the PLOT column. In addition, all 5 in-gel digested fractions were combined together to represent a global proteomic analysis for characterization of the PLOT column.

Compared to silica-based stationary phases, organic polymeric stationary phases provide several advantages, e.g., improved chemical stability over an extended pH range and the absence of silanol groups that can cause irreversible adsorption of peptides and proteins. The exemplary PS-DVB porous layer was prepared and attached to the silanized capillary wall in a single in situ copolymerization step. Selection of a suitable solvent for the copolymerization step is key to successful preparation of repeatable, high efficiency PLOT columns. The polymer should precipitate from solution at an early stage of the polymerization process, forming a thin porous layer at the capillary wall, while leaving open the main section of the capillary tube. A porogenic solvent in which the resulting polymer, e.g., PS-DVB, is not very soluble is, therefore, desirable for the preparation of the PLOT column.

Several organic solvents, including methanol, ethanol, propanol, tetrahydrofuran, and acetonitrile, were examined for their ability to prepare repeatable PLOT columns. From this group, the non-polar solvent ethanol was selected for further study since successful columns were routinely made using this solvent. The effect of the ratio of ethanol to monomer concentration on the preparation of the PLOT column was then investigated. In these studies, more than 50% monomer in the polymerization mixture was observed to lead to column blockage. At 60% ethanol/40% monomer, repeatable, high performance PLOT columns were obtained.

Figure 2A:
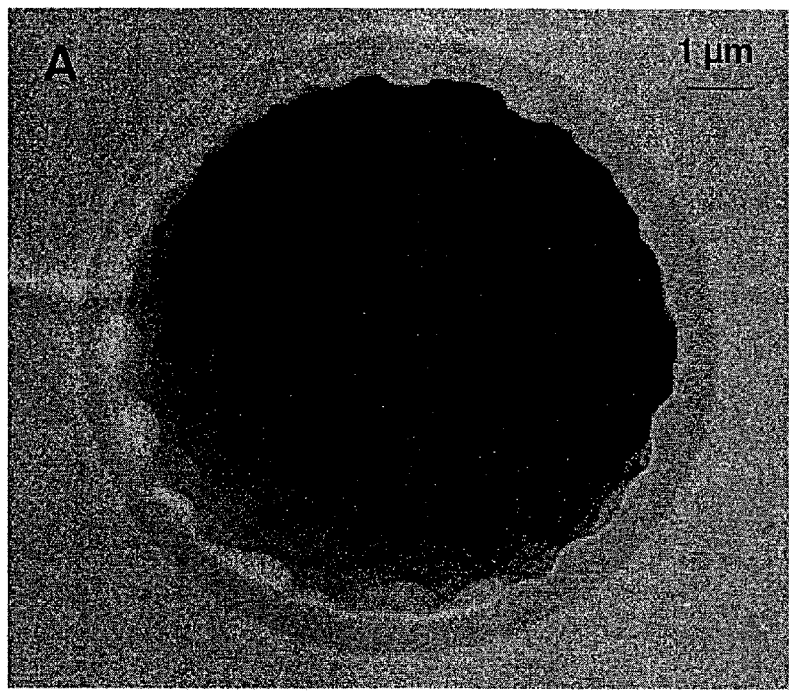
FIGS. 2A and 2B are scanning electron micrographs of the middle section (A) of the PLOT column of FIG. 1 and of an end section (B) of the PLOT column. The end sections constitute roughly 5% of the approx. 5 m long capillary.
Figure 2B:
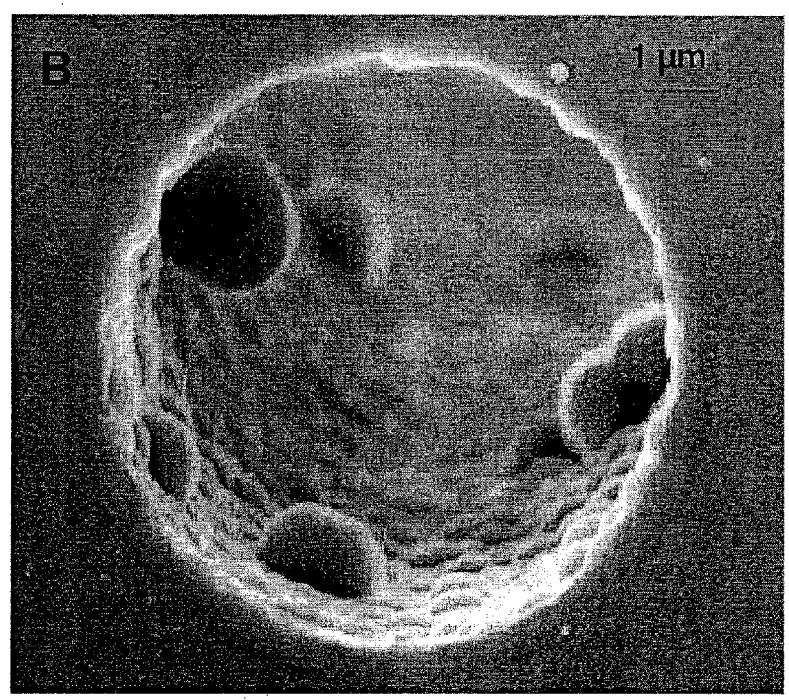
Figure 3A:
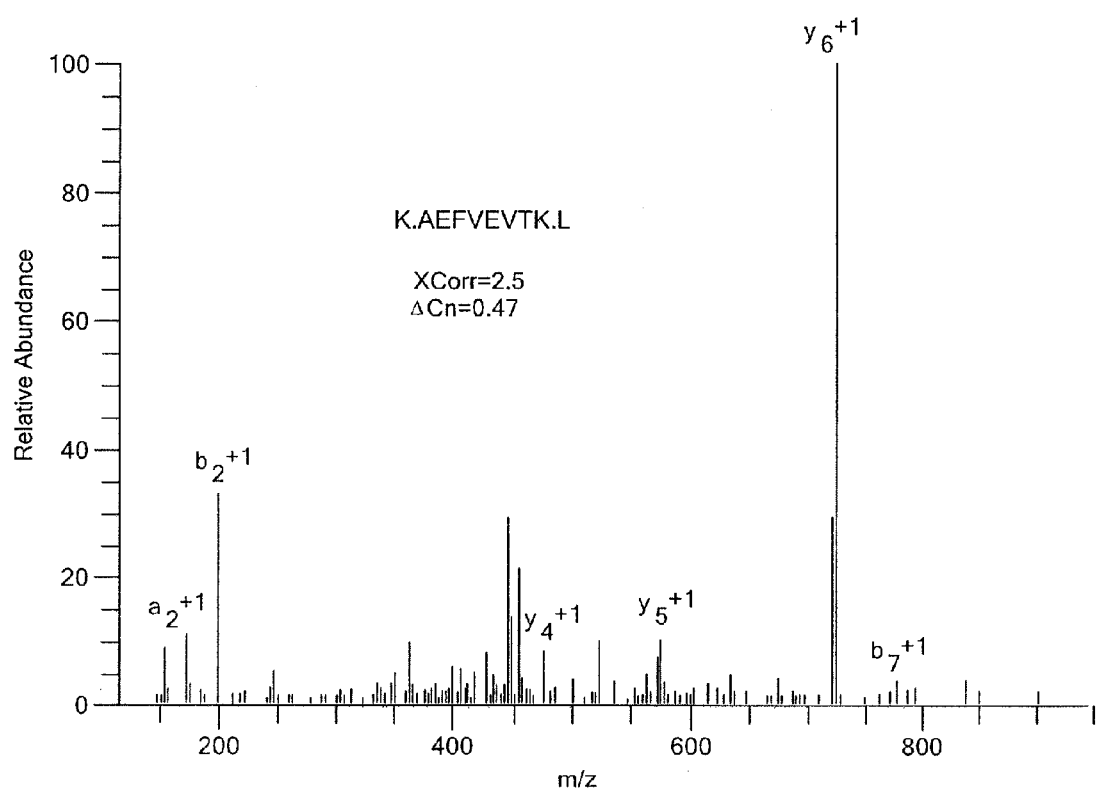
FIGS. 3A-3D are MS/MS spectra from four peptides of a BSA tryptic digest with 10 attomole injected directly onto the PLOT column.
Figure 3B:
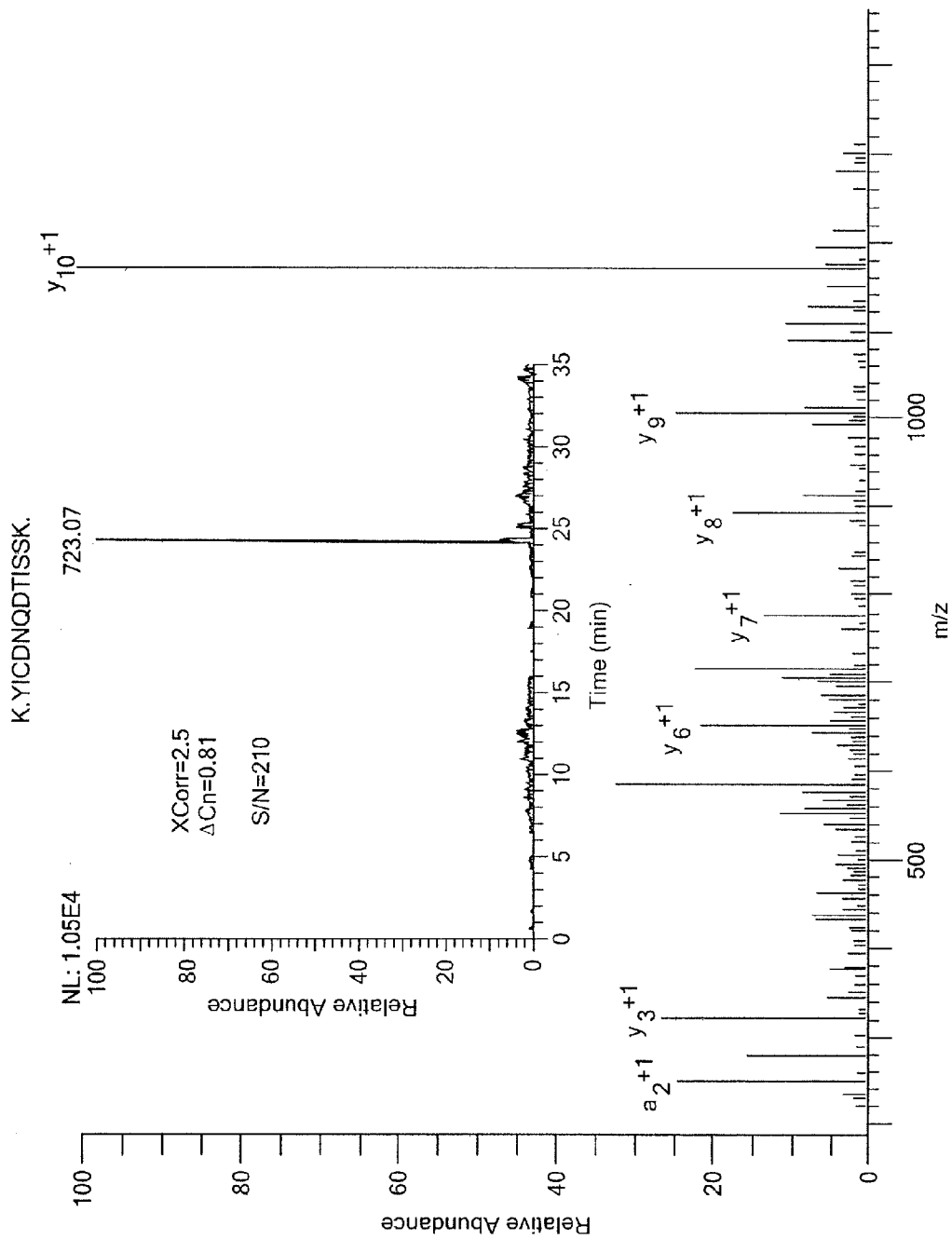
Figure 3C:
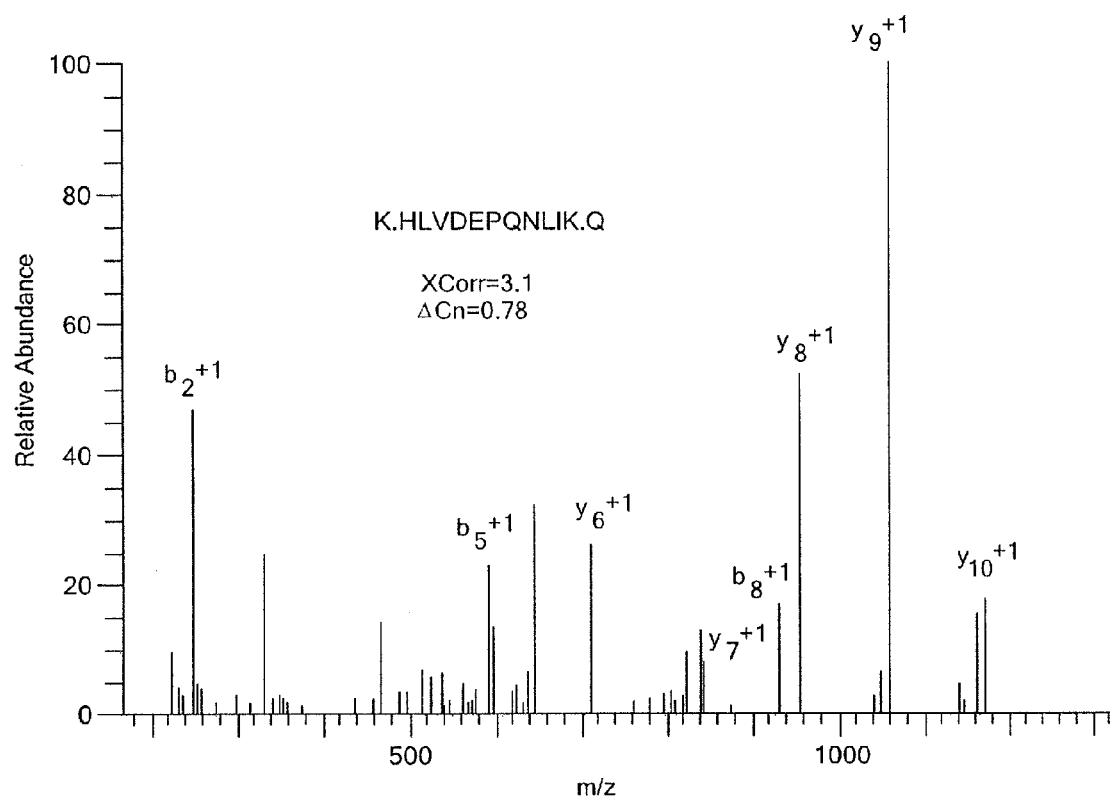
Figure 3D:
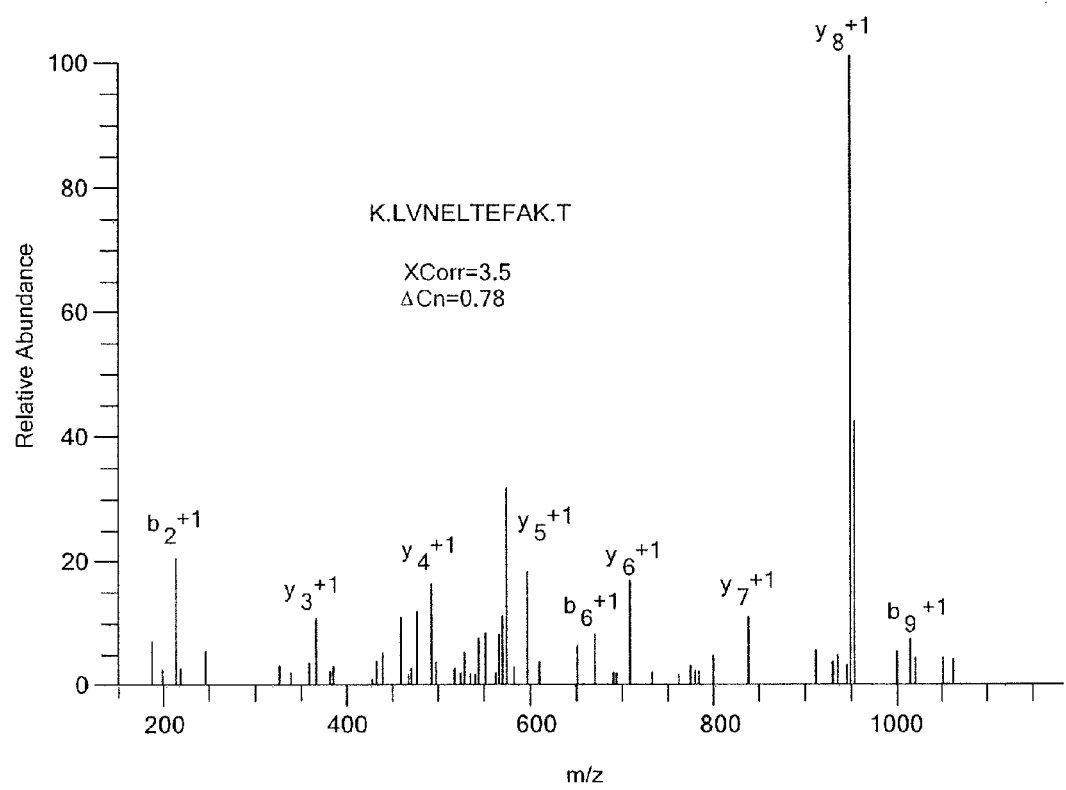

The surface layer of a PLOT column, prepared from ~5 meter of 10 μm i.d. fused silica capillary tubing using 60% ethanol, was then examined at different sections of the column using scanning electron microscopy (SEM). Referring to FIG. 2A, it can be seen that the porous layer was observed to be uniform throughout most of the capillary. Portions at the ends of the capillary (~5% from each end) contained relatively large globules, as shown in FIG. 2B. These ends are cut to produce a column of length ~4.2 meters. From the SEM picture, the thickness of the surface inner layer of the PLOT column was estimated to be between 0.5 and 1 μm. Since there may be some globules interspersed at low density throughout the column, the average thickness may be somewhat higher. Earlier experiments had suggested that the layer thickness should be in the range 0.3-2 μm for a coated open tubular column, depending on the mass transfer coefficients of the solutes between the mobile and stationary phases[40].

Example II

Characterization of Column Performance

A variety of chromatographic studies were conducted to characterize a 4.2 m×10 μm i.d. PLOT column accordng to the invention. The long column provided a flow rate of ~20 L/min at pressures of only ~2900 psi. On the basis of these conditions, Darcy's law[41] was used to calculate the column permeability as $1.3 \times 10^{-12}$ m$^2$. It is interesting to note that this value is roughly 4-fold lower than an equivalent open tube capillary of 10 μm i.d. without a porous layer. The lower permeability and higher pressure drop of the PLOT column according to the invention is undoubtedly due to the porous layer reducing the open tube diameter. On the other hand, the permeability is 15-fold higher than a recently introduced 10 μm i.d. silica monolithic column[16]. Thus, the column according to the invention is characterized by relatively high permeability in comparison to a similarly sized packed column. Hence, very long columns according to the invention, e.g., of 4 m or greater, can be operated successfully with commercially available HPLC pumping systems that have a pressure limit of 6000 psi.

Use of a detection system and associated connections that make only a minimal contribution to extra column dead volume is the key to achieve high efficiency separation of narrow bore PLOT column at such low flow rates[42]. In this study, a PicoClear union was used to connect the PLOT column and the ESI emitter. Through visual inspection, the straight cut PLOT column outlet was observed to be closely connected to the coated ESI emitter, which had a 5 μm i.d. spray tip, 2-3 cm long. The emitter could be easily replaced if the tip became clogged. Stable electrospray was readily generated from the emitter at flow rates of ~20 nL/min.

Since the columns of the invention are made in a single step after silanization of the capillary wall, a simple procedure for column production can be established. Reproducibility of retention from column to column was tested in the gradient elution separation of a 1:1 mixture of a BSA tryptic digest and a β-casein Lys-C digest. An 800-attomole amount of the mixture was bomb loaded on the PLOT column. High-performance separation was carried out with direct loading and use of a microSPE column. Gradient: mobile phase A (0.1% (v/v) formic acid in water) to 40% B (0.1% (v/v) formic acid, 10% (v/v) water in acetonitrile) in 45 min with data collection initiated at the start of the gradient. Flow rate: ~20 nL/min at an inlet pressure of ~2900 psi. The run-to-run retention time reproducibility was established from three independent analyses. The consecutive run-to-run reproducibility was found to be better than 1.2% RSD. Three, separate PLOT columns were then prepared, and the reproducibility of retention from column-to-column is presented in Table 1.

TABLE 1

PLOT Column-to-Column Reproducibility[a]

| | Retention time (min) | | | | |
|---|---|---|---|---|---|
| m/z | Column 1 | Column 2 | Column 3 | RSD, % | RSD*, %[b] |
| 655 | 33.84 | 34.83 | 36.11 | 3.26 | 1.97 |
| 480 | 34.21 | 35.10 | 36.41 | 3.14 | 1.81 |
| 582 | 34.97 | 35.86 | 37.27 | 3.21 | 1.83 |
| 813 | 35.50 | 36.35 | 37.48 | 2.73 | 1.56 |
| 628 | 37.62 | 38.26 | 39.55 | 2.55 | 1.22 |
| 741 | 39.01 | 39.62 | 40.96 | 2.51 | 1.15 |
| 879 | 41.57 | 41.93 | 43.36 | 2.24 | 0.77 |
| 843 | 42.05 | 42.74 | 44.12 | 2.45 | 1.16 |
| 785 | 43.20 | 43.85 | 45.52 | 2.71 | 1.22 |
| 832 | 47.46 | 47.55 | 49.42 | 2.30 | 0.50 |
| 1340 | 50.62 | 50.13 | 52.11 | 2.02 | 0.18 |
| 1330 | 52.05 | 51.43 | 53.38 | 1.91 | 0.34 |
| 1241 | 52.79 | 52.47 | 54.46 | 2.01 | — |

[a]Mixture of BSA tryptic digest and β-casein Lys-C digest was used to test the column-to-column reproducibility of three 4.2 m × 10 µm i.d. PS-DVB PLOT columns.
[b]RSD* represents the RSD of relative retention time normalized to the ion of m/z = 1241.

It can be seen that the reproducibility for the three columns was better than 3% RSD, and if the retention was normalized to the ion with m/z=1241, the RSD drops to less than 2%. The results in Table 1 are very promising given that the tube diameter was only 10 µm i.d. A likely source of the larger column-to-column % RSD relative to that for the run-to-run retention reproducibility is minor differences in flow rate resulting from small variations in column permeability. The average peak width for six high-intensity m/z peaks on the three columns was also determined. The peak width at half-height was 6±0.5 s on the three PLOT columns, again indicating good reproducibility. Finally, the PLOT columns showed good stability. The retention and peak widths remained unchanged over 3 months, with hundreds of sample injections.

The loading capacities of the PLOT column were determined by measuring peak width at half-height ($w_{1/2}$) as a function of injected amounts of angiotensin I (1296.5 Da) and insulin (5733.5 Da). The maximum loading capacity is defined as the amount of sample injected when the corresponding $w_{1/2}$ is increased by 10% over the peak width at low sample amounts. Using a fixed sample volume of 2 nL, the sample solution at various concentrations was bomb loaded on the PLOT column. NanoLC-ESI-MS was conducted with a 20 min gradient, and the $w_{1/2}$ for each analysis was determined from the corresponding extracted ion chromatogram. The loading capacities of the PLOT column, prepared using 60% of solvent, were ~100 fmol for angiotensin I and ~50 fmol for insulin. Given that 10 µm i.d. columns were used, these values represent relatively high loading capacity.

It is useful to compare these results to the loading capacity of a 6 cm×200-µm-i.d. PS-DVB monolithic column (column volume of ~1.9 µL) of ~1 µmol, previously reported for a small peptide[42]. The column volume of the 4.2 m×10-µm-i.d. PLOT column was ~0.33 µL, or roughly 20% that of the above monolithic column. Thus, on a column volume basis, the loading capacity of the PLOT column differed from the 200 µm i.d. monolithic column by only a factor of 2 as a result of the long column length. The loading capacities of the PLOT column prepared using 70% ethanol decreased to ~50 fmol for angiotensin I and ~20 fmol for insulin. The higher percentage of ethanol resulted in the PS-DVB polymer phase separation occurring at an earlier stage of polymerization, likely leading to less polymer coated on the tubing wall and thus a lower loading capacity.

The ultimate goal of narrow bore LC-ESI-MS is to achieve low detection limits without sacrificing separation performance. The detection level achievable with the PLOT column of the invention was evaluated using a tryptic digest of bovine serum albumin (BSA). Ten attomoles of a BSA tryptic digest was bomb loaded directly onto the 10 µm i.d. PLOT column and detected by the linear ion trap MS. Four peptides that provided good MS/MS fragmentation and high SEQUEST scores were confidently identified, as shown in FIGS. 3A-3D. The extracted ion chromatogram of the peptide (YICDNQDTISSK) with the highest MS response (signal-to-noise ratio ~210) is shown in the insert to FIG. 3B, indicating that the detection limit for this peptide can, in principle, be in the hundreds of zmole range.

Example III

Comprehensive Analysis of Large Complex Peptide Fragments of EGFR

High sequence coverage proteomic analysis and comprehensive characterization of post-translational modifications at the trace level are particularly important to help to address a variety of problems of biological interest. Often, one is faced with a limited amount of sample and, yet it can be important to determine and quantitate individual protein isoforms. An intermediate approach between top down and bottom up proteomics, extended range proteomic analysis (ERPA), was recently introduced for comprehensive characterization of complex proteins[44]. Lys-C was used as the proteolytic enzyme instead of trypsin, since the former enzyme is a less frequent cutter. Thus, the complexity of the sample was reduced (~2-3 fold lower number of peptide fragments than for trypsin). The Lys-C digest, on average, led to longer peptides than that for the tryptic digest. In addition, extra arginines were frequently included in the digest fragment, leading to enhanced signal for post-translationally modified peptides. Using this approach, greater than 95% sequence coverage was demonstrated in the analysis of a phosphorylated and glycosylated tyrosine kinase receptor, EGFR, at the 75-fmole level using a 50-µm monolithic column[45].

Figure 4A:
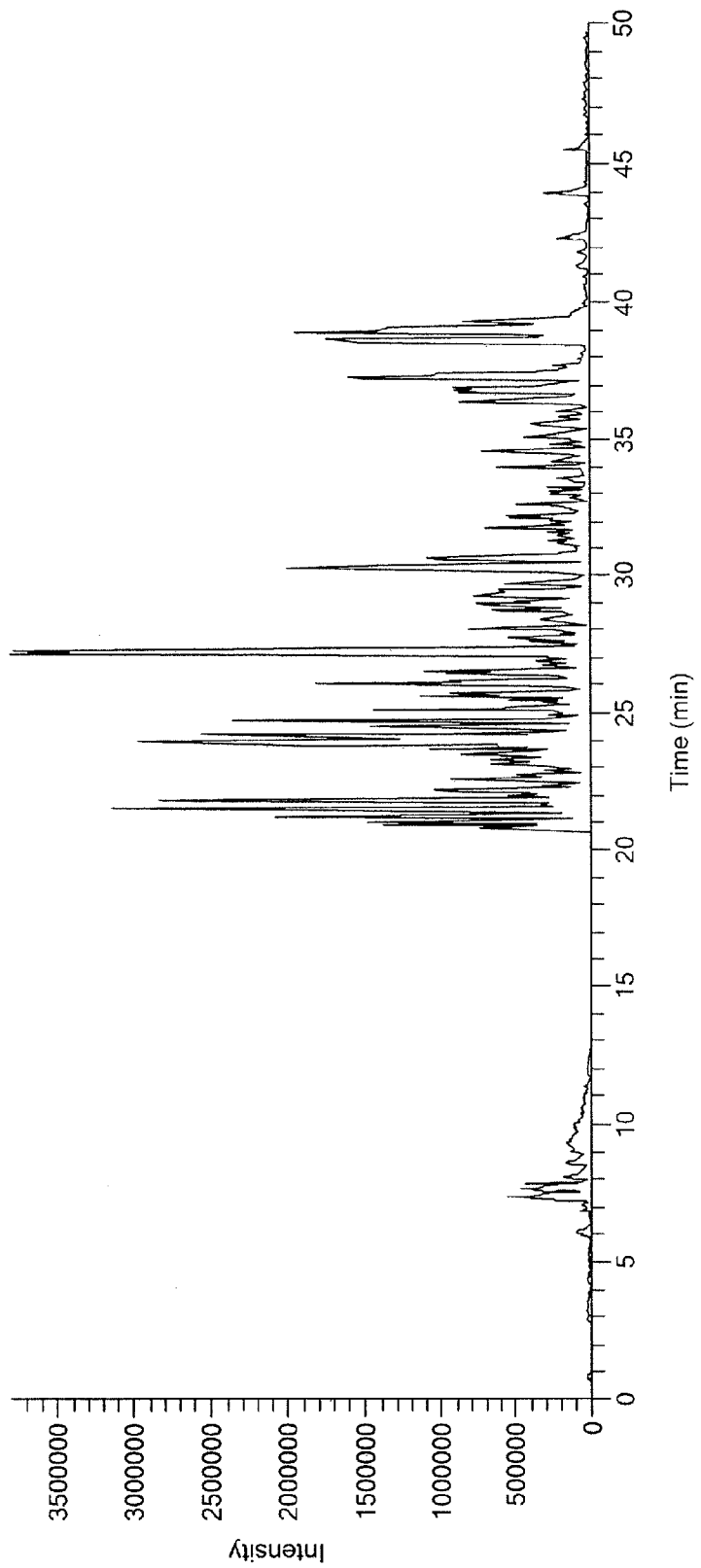
FIGS. 4A-4E illustrate comprehensive analysis of a Lys-C digest of EGRF. (A) Base peak chromatogram from nanoLC-ESI-MS analysis of 25 fmol of a Lys-C digest of EGFR injected on the 4.2 m×10 μm i.d. PS-DVB PLOT column according to the invention; selected MS/MS spectra are shown for long (B), phosphorylated (C), and glycosylated (D, E) peptides of EGFR. The peptide sequences and the extracted ion chromatograms are shown in the insert. The phosphothreonine is indicated as T*. The glycosylation site is labeled N*. In the Man8 structure, the triangle (▲) and circle (●) represent mannose and N-acetyl glucosamine, respectively. The sequential loss of terminal mannoses from the Man8 structure resulted in Man7, Man6, etc. In the glycan structures, SA represents sialic acid and the square (■) represents galactose.
Figure 4B:
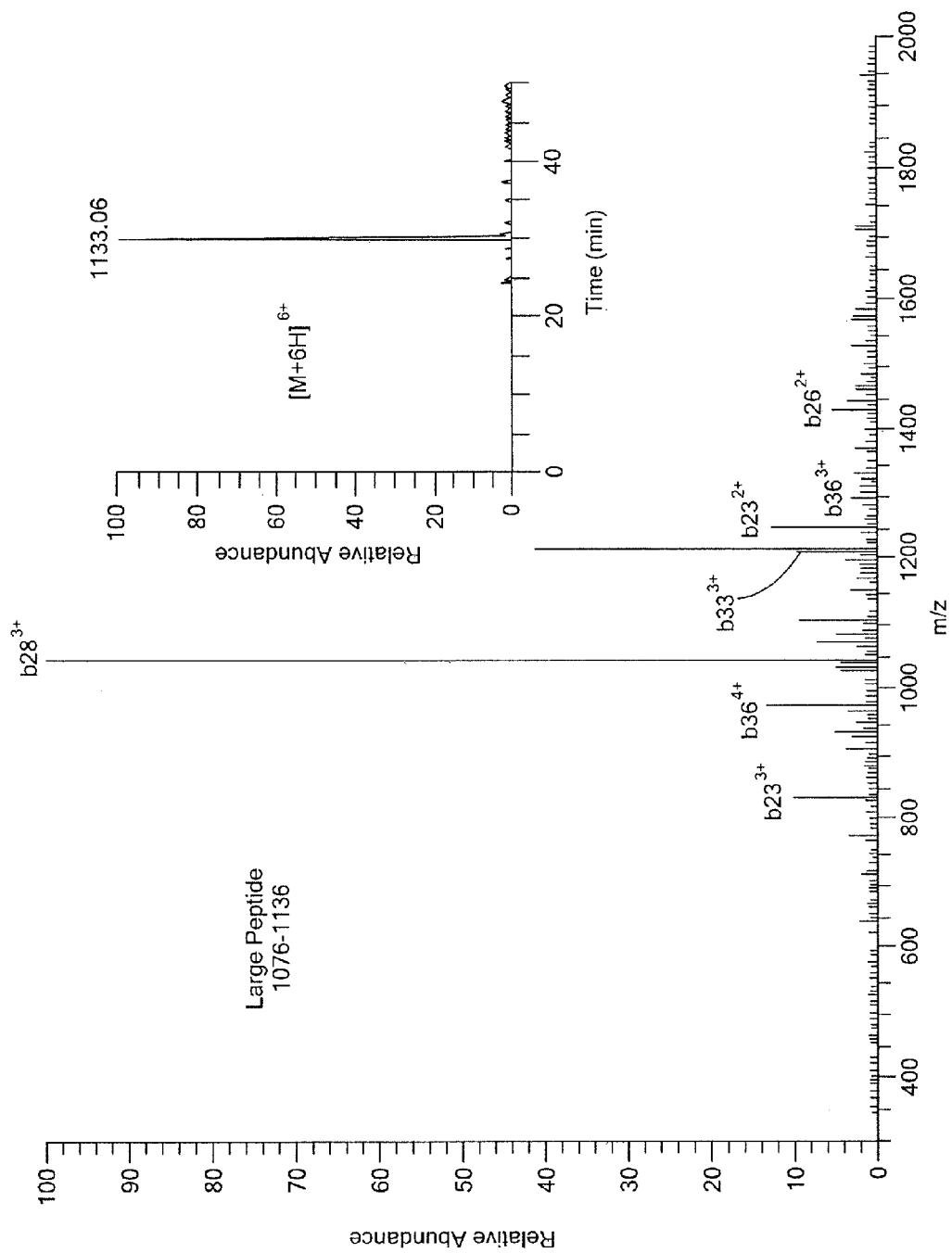
Figure 4C:
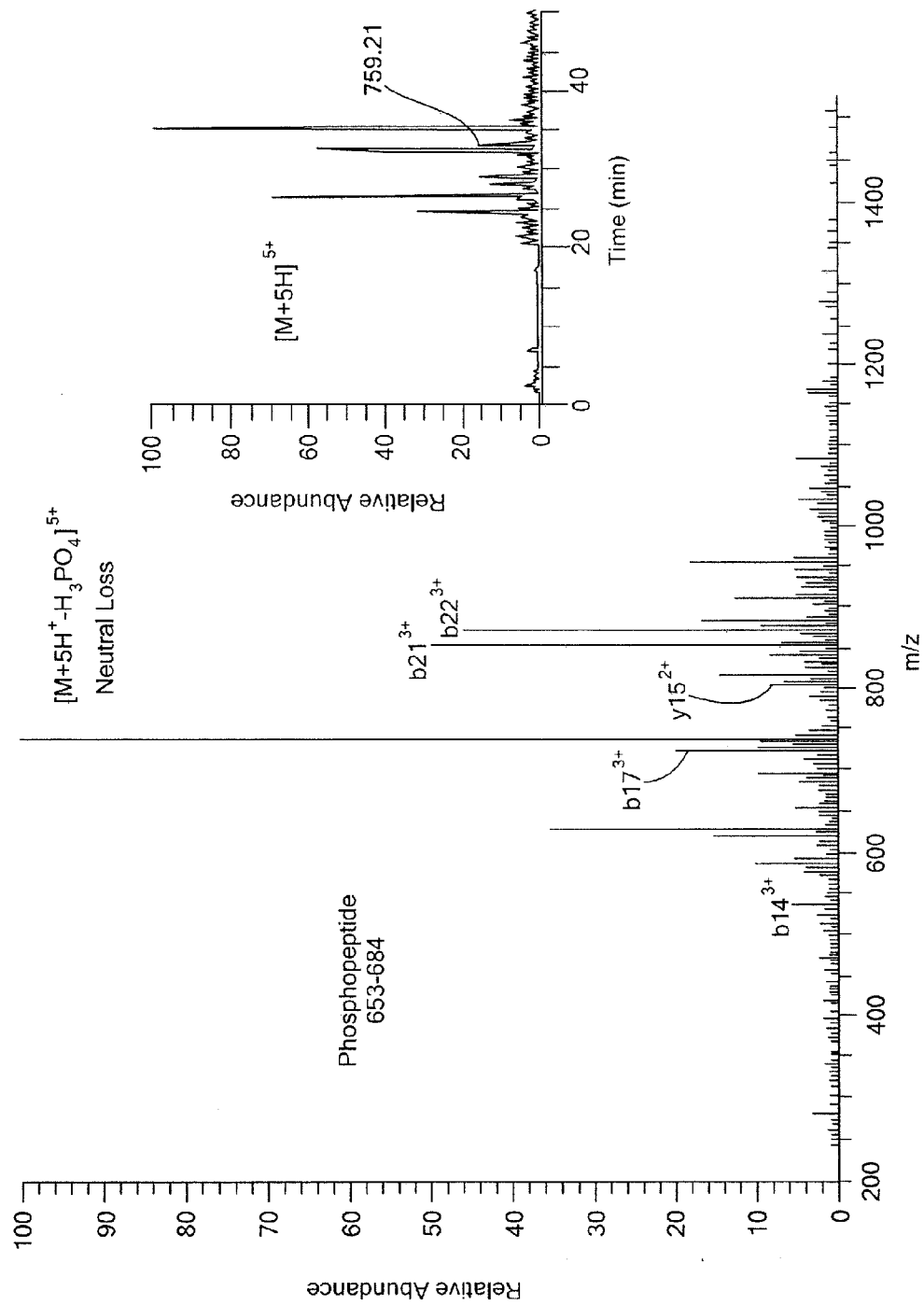

Due to its open porous structure and high sensitivity features, PLOT columns according to the invention can also be effective for the analysis of large post-translationally modified peptides, such as found with the ERPA approach. As a comparison with the earlier work, FIG. 4A shows the base peak separation of ~25 fmol Lys-C digest of EGFR on the 4.2 m×10 µm i.d. PLOT column. On the basis of MS/MS analysis and to manually match previously identified peptides[44], >70%, sequence coverage, including post-translational modifications, was obtained. As an example, FIG. 4B illustrates the MS/MS spectra of a large peptide, as well as phosphorylated and glycosylated peptides and their extracted ion chromatograms. As seen in the figure, using a 45 min. linear gradient, symmetrical and narrow peaks were observed for the large peptide ($w_{1/2}$, 7 s) (FIG. 4), phosphopeptide ($w_{1/2}$, 9 s) (FIG.

Figure 4D:
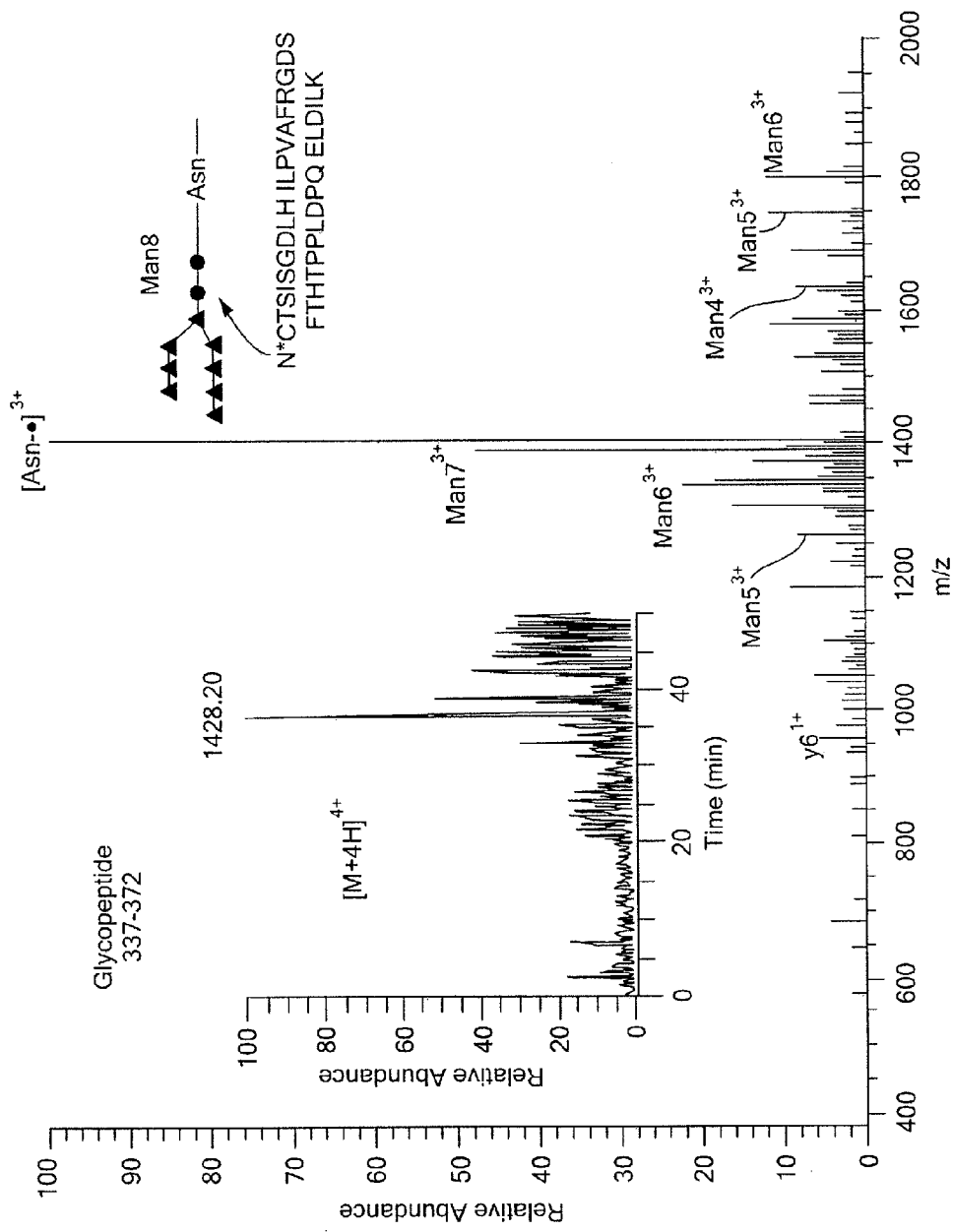
Figure 4E:
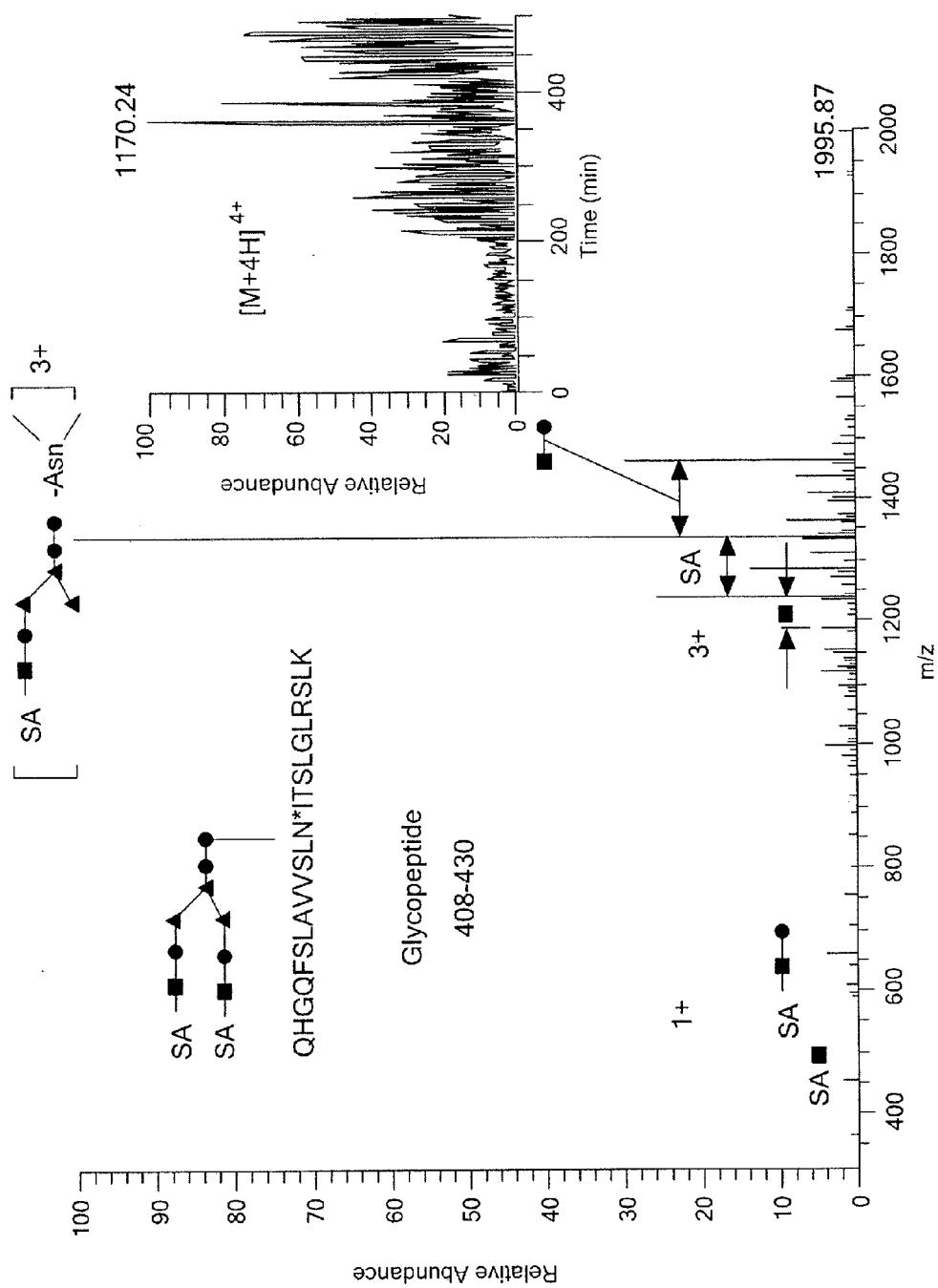

4C), and glycopeptides ($w_{1/2}$, ~10s) (FIGS. 4D and 4E). The PLOT column demonstrated high efficiency for the separation of all Lys-C digest peptides of EGFR. The PLOT columns according to the invention should be effective for even larger fragments, including intact proteins.

Example IV

MicroSPE/nanoLC/ESI-MS Analyses

Successful practical operation of the PLOT column according to the invention requires the ability to handle samples of at least of few microliters volume. Since direct injection of such sample volumes on the PLOT column would take a long time, if successful at all, precolumn enrichment is an important procedure for sample handling. In addition, use of a precolumn would allow successful removal of salts and other species in the sample solution that are deleterious to ESI-MS. Following established procedure[46], the sample was pressure loaded manually on a 4 cm×50 µm i.d. PS-DVB monolithic precolumn. Flows of ~0.5 µL/min at a pressure of ~1000 psi were used for loading on the precolumn, such flow rates being ~25× greater than that for direct loading on the PLOT column. After loading, the precolumn was then inverted and butt-to-butt connected to the PLOT column using a PicoClear union. An important feature of the union is that it can hold pressure up to 5000 psi. The sample, loaded on the precolumn, was then back-flushed onto the PLOT column. Automated loading of a precolumn and sample injection are also within the invention.

Figure 5A:
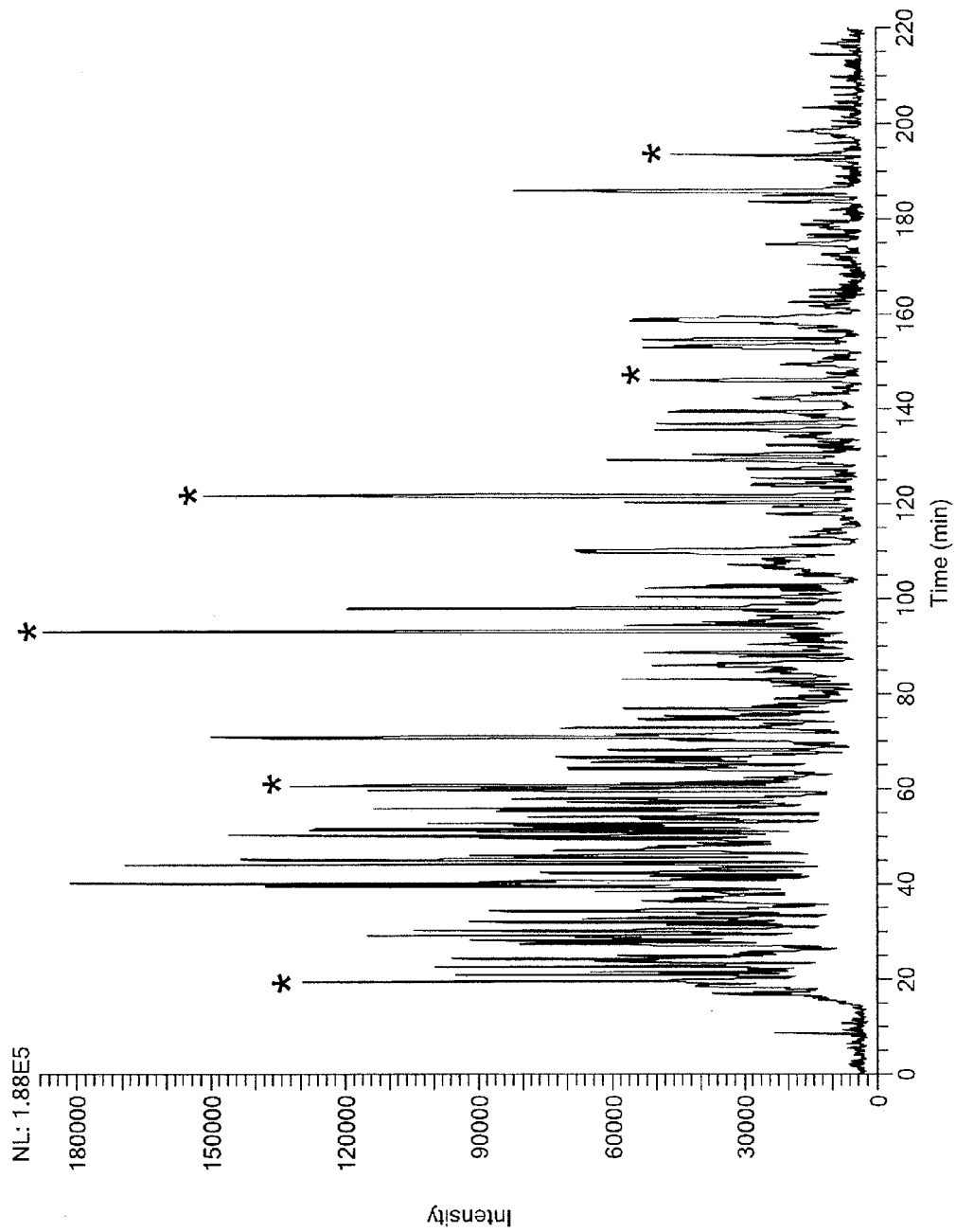
FIGS. 5a and 5B are chromatograms providing for the calculation of peak capacity for the column according to FIG. 1.
Figure 5B:
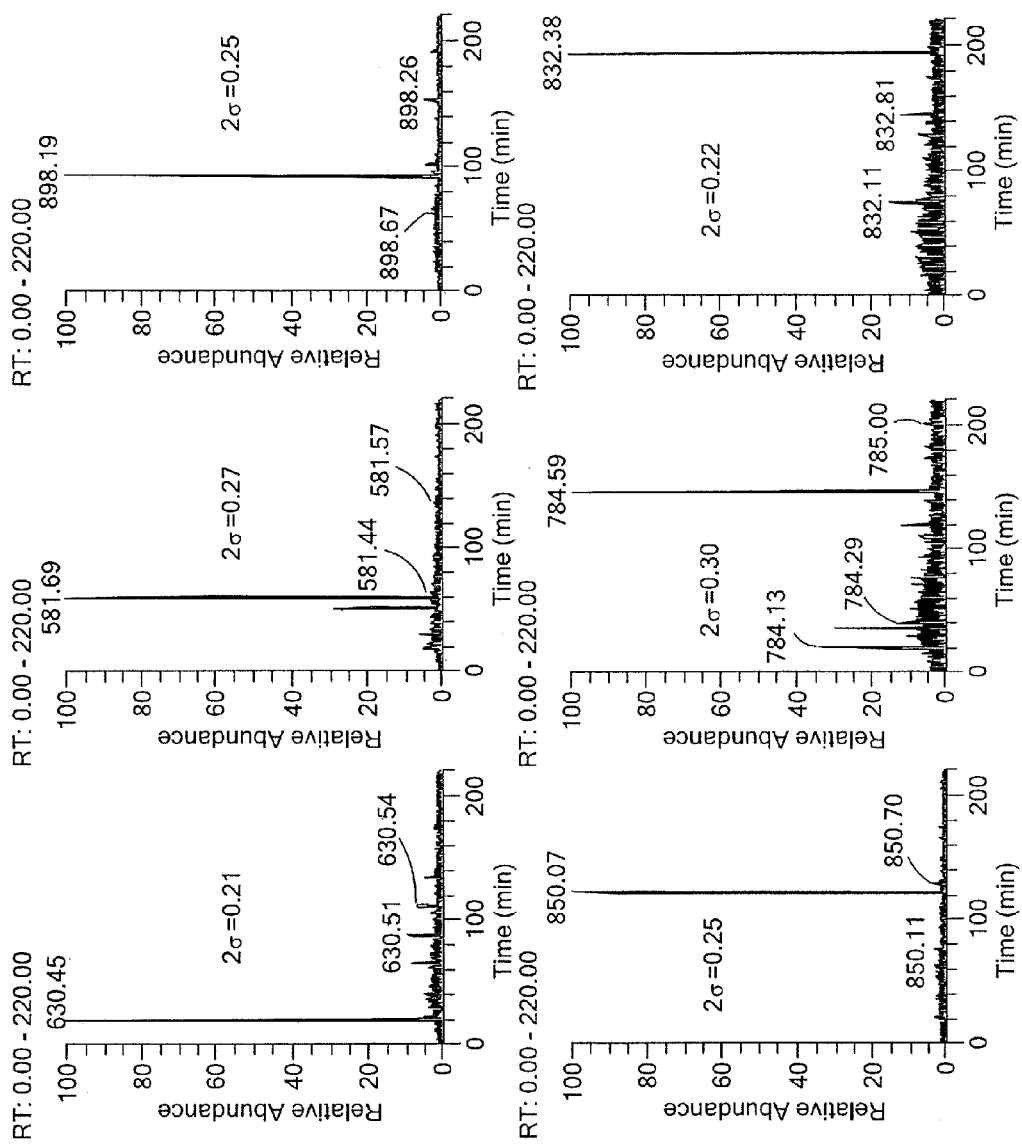

The resolving power of the microSPE-nanoLC-ESI-MS system was evaluated using an in-gel tryptic digest of a proteomic sample of the archaeon, *M. acetivorans*. First, a 1 µL sample was loaded onto a 4 cm×50 µm i.d. PS-DVB monolithic precolumn using a pressure bomb at a flow rate of 0.5 µL/min. FIG. 5A shows a 3.5-h gradient separation of only 4 ng of an in-gel tryptic digest sample of a gel fraction (>70 kDa) of *M. acetivorans* on the 4.2 m×10 µm i.d. PLOT column. The base peak chromatogram in FIG. 5A illustrates both the complexity of the sample and the high resolving power of the system, with symmetrical peaks being observed throughout the entire separation. The peak capacity of the gradient separation using the PLOT column was estimated by examining the extracted ion chromatograms of individual components throughout the separation window (FIG. 5B)[47]. The 26 values of six high intensity peaks over the wide gradient range are between 0.21 and 0.30 s, leading to an estimation of peak capacity of ~400. Even higher peak capacities are anticipated with full system optimization. A total of 689 unique peptides and 238 proteins (single-hit peptides excluded) were identified from this very small sample. The peptides and proteins were identified by automated searching of MS/MS spectra of the *M. acetivorans* database. The number of identified peptides and proteins increased significantly, from 689 and 238 to 1793 and 512, respectively, as the injection amount was increased from 4 ng to 50 ng. Given that the sample was prepared by in-gel digest[47], 50 ng is still a relatively limited amount of material.

Finally, as a test the system of the invention, the five in-gel digested fractions were combined together to simulate a global proteomic sample. For three repeat gradient runs from 150 ng of the combined in-gel digest of *M. acetivorans*, a total of 4409 unique peptides and 715 different proteins (single hits excluded) were identified. These results demonstrate the potential of the system of the invention for high resolution analysis with a limited sample amount.

REFERENCES

1. Aebersold, R.; Goodlett, D. R. *Chem. Rev.* 2001, 101, 269-295.
2. Washburn, M. P.; Wolters, D.; Yates, J. R. *Nature Biotechnol.* 2001, 19, 242-247.
3. Smith, R. D.; Anderson, G. A.; Lipton, M. S.; Pasa-Tolic, L.; Shen, Y.; Conrads, T. P.; Veenstra, T. D.; Udseth, H. R. *Proteomics* 2002, 2, 513-523.
4. Bonner, R. F.; EmmertBuck, M.; Cole, K.; Pohida, T.; Chuaqui, R.; Goldstein, S.; Liotta, L. A. *Science* 1997, 278, 1481-1483.
5. Smith, R. D.; Shen, Y. F.; Tang, K. Q. *Accounts Chem. Res.* 2004, 37, 269-278.
6. Ivanov, A. R.; Zang, L.; Karger, B. L. *Anal. Chem.* 2003, 75, 5306-5316.
7. Shen, Y. F.; Moore, R. J.; Zhao, R.; Blonder, J.; Auberry, D. L.; Masselon, C.; Pasa-Tolic, L.; Hixson, K. K.; Auberry, K. J.; Smith, R. D. *Anal. Chem.* 2003, 75, 3596-3605.
8. Luo, Q.; Shen, Y.; Hixson, K. K.; Zhao, R.; Yang, F.; Moore, R. J.; Mottaz, H. M.; Smith, R. D. *Anal. Chem.* 2005, 77, 5028-5035.
9. Cech, N. B.; Enke, C. G. *Mass Spectrom. Rev.* 2001, 20, 362-387.
10. Tang, L.; Kebarle, P. *Anal. Chem.* 1993, 65, 3654-3668.
11. Wilm, M.; Mann, M. *Anal. Chem.* 1996, 68, 1-8.
12. Patel, K. D.; Jerkovich, A. D.; Link, J. C.; Jorgenson, J. W. *Anal. Chem.* 2004, 76, 5777-5786.
13. Svec, F.; Frechet, J. M. J. *Anal. Chem.* 1992, 64, 820-822.
14. Premstaller, A.; Oberacher, H.; Huber, C. G. *Anal. Chem.* 2000, 72, 4386-4393.
15. Minakuchi, H.; Nakanishi, K.; Soga, N.; Ishizuka, N.; Tanaka, N. *Anal. Chem.* 1996, 68, 3498-3501.
16. Luo, Q.; Tang, K.; Yang, F.; Elias, A.; Shen, Y.; Moore, R. J.; Zhao, R.; Hixson, K. K.; Rossie, S. S.; Smith, R. D. *J. Proteome Res.* 2006, 5, 1091-1097.
17. Berkel-Geldof, O. V.; Kraak. J. C.; Poppe H. *J. Chromatogr.* 1990, 499, 345-359.
18. Tsuda, T.; Nakagawa, G. *J. Chromatogr.* 1983, 268, 369-374.
19. Halasz, I.; Horvath, C. *Nature* 1963, 191, 71-71.
20. Kennedy, R. T.; Jorgenson, J. W. *Science* 1989, 246, 75-82.
21. Knox, J. H.; Gilbert, M. T. *J. Chromatogr.* 1979, 186, 405-418.
22. Tijssen, R.; Bleumer, J. P. A.; Van Kreveld M. E. *J. Chromatogr.* 1983, 260, 297-304.
23. Guiochon, G. *Anal. Chem.* 1981, 53, 1318-1325.
24. Swart, R.; Kraak, J. C.; Poppe, H. *J. Chromatogr.* 1995, 689, 177-187.
25. Gohlin, K.; Larsson, M. *J. Chromatogr.* 1993, 645, 41-56.
26. Tock, P. P. H.; Boshoven, C.; Poppe H.; KraakK. J. C.; Unger, K. *J. Chromatogr.* 1989, 477, 95-106.
27. Yun, H.; Markides, K. E.; Lee, M. L. *J. Microcol. Sep.* tember 1995, 7, 153-158.
28. Dluzneski, P. R.; Jorgenson, J. W. *J. High Resout. Chromatogr. Chromatogr. Commun.* 1988, 11, 332-336.
29. Guo, Y.; Colon, L. A. *Anal. Chem.* 1995, 67, 2511-2516.
30. Liu, F.; Hsu, Y.; Wu, C. *J. Chromatogr. A* 2005, 1083, 205-214.
31. Yang, L.; Guihen, E.; Holmes, J. D.; Loughran, M.; O'Sullivan, G. P.; Glennon, J. D. *Anal. Chem.* 2005, 77, 1840-1846.

32. Ruan, Z. Q.; Liu, H. X. *J. Chromatogr. A* 1995, 693, 79-88.
33. Huang, X.; Zhang, J.; Horvath, C. *J. Chromatogr. A* 1999, 858, 91-101.
34. Shen, T. *J. Chromatogr. Sci.* 1992, 30, 239-240.
35. Hulthe, G.; Petersson, M. A.; Fogelqvist, E. *Anal. Chem.* 1999, 71, 2915-2921.
36. Bakry, R.; Gjerde, D.; Bonn, G. K. *J. Proteome Res.* 2006, 5, 1321-1331.
37. Li, Q.; Li, L.; Rejtar, T.; Karger, B. L.; Ferry, J. *J. Proteome Res.* 2005, 4, 112-118.
38. Viklund, C.; Svec, F.; Frechet, J. M. J.; Irgum, K. *Chem. Mater.* 1996, 8, 744-750.
39. Svec, F.; Frechet, J. M. *J. Chem. Mater.* 1995, 7, 707-715.
40. Poppe H.; Kraak. J. C. *J. Chromatogr.* 1983, 255, 395-414.
41. Hlushkov, D.; Tallarek, U. *J. Chromatogr., A* 2006, 1126, 70-85.
42. Liu, G.; Svenson, L.; Djordjevic, N.; Erni, F. *J. Chromatogr.* 1993, 633, 25-30.
43. Premstaller, A.; Oberacher, H.; Walcher, W.; Timperio, A. M.; Zolla, L.; Chervet, J. P.; Cavusoglu, N.; van Dorsselaer, A.; Huber, C. G. *Anal. Chem.* 2001, 73, 2390-2396.
44. Wu, S.; Kim, J.; Hancock, W. S.; Karger, B. L. *J. Proteome Res.* 2005, 4, 1155-1170.
45. Wu, S.; Kim, J.; Bandle, R. W.; Liotta, L.; Petricoin E.; Karger, B. L. *Mol. Cell. Proteomics* 2006, ASAP.
46. Martin, S. E.; Shabanowitz, J.; Hunt, D. F.; Marto, J. A. *Anal. Chem.* 2000, 72, 4266-4274.
47. Wang, X.; Barber, W. E.; Carr, P. W. *J. Chromatogr. A* 2006, 1107, 139-151.
48. Havlis, J.; Shevchenko, A. *Anal. Chem.* 2004, 76, 3029-3036.
49. Knox, J H and Gilbert, M T. *J. Chromatogr.*, 186 (1979) 405-418.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A process for carrying out a chemical analysis method on a sample, said method comprising the steps of:
   providing a porous layer open tube (PLOT) capillary column, or channel in a microfabricated device, said column or channel comprising:
      a capillary column or channel having an i.d. of 15 μm or less, an entrance end and an exit end;
      a rigid porous layer separation medium comprising a highly crosslinked, macroporous, organic polymeric stationary phase layer covalently attached to the inner wall surface of said column or channel, wherein said organic polymeric stationary phase layer is from 0.5-3 μm in thickness, and wherein the reproducibility of retention time on comparable said columns or channels during use in high performance liquid chromatography varies less than 10%; and
      an open unfilled bore inside said rigid porous layer, wherein said open bore is disposed around a central axis of said column or channel and extends the length of said column or channel;
   coupling a mass flow or concentration sensitive detector via an interface to the exit end of said column or channel, wherein said interface is an electrospray ionization (ESI) interface or a matrix assisted laser desorption ionization (MALDI) interface;
   applying an aliquot of a liquid sample to said column or channel;
   conducting a high performance liquid chromatographic separation procedure on said applied sample; and
   detecting said separated sample with said detector to carry out said chemical analysis method.

2. The process of claim 1, wherein the reproducibility of retention time on comparable said columns or channels during use for said high performance liquid chromatographic separation procedure varies less than 5%.

3. The process of claim 1, wherein said high performance liquid chromatographic separation procedure is conducted at a flow rate of 5-50 nL/min.

4. The process of claim 1, wherein said column or channel during said high performance liquid chromatographic separation procedure has a flow rate of 5-50 nL/min. at 6000 psi or less.

5. The process of claim 1, wherein said column has a length of greater than or equal to three meters.

6. The process of claim 1, wherein, in said column or channel, said organic polymeric stationary phase layer attached to the inner wall surface of said column or channel comprises styrene and divinylbenzene monomer units.

7. The process of claim 1, wherein, in said column or channel, said organic polymeric stationary phase layer attached to the inner wall surface of said column or channel comprises (C4-C18) alkyl methacrylate monomer units.

8. The process of claim 1, wherein said detector is a mass spectrometer, a fluorescence detector, an electro-chemiluminescence detector or a nuclear magnetic resonance detector.

9. The process of claim 1, wherein said interface is an electrospray ionization (ESI) interface and said detector is a mass spectrometer.

10. The process of claim 1, wherein said interface is a matrix assisted laser desorption ionization (MALDI) interface and said detector is a mass spectrometer.

11. The process of claim 1, said process further comprising coupling a preparatory precolumn to the entrance end of said separation column or channel and applying said aliquot of said liquid sample to said preparatory precolumn.

12. The process of claim 1, wherein said organic polymeric stationary phase layer comprises styrenic, methacrylic or acrylic monomeric units, or combinations thereof.

13. The process of claim 1, wherein said organic polymeric stationary phase layer is thermally stable to 250° C.

* * * * *